United States Patent [19]
Abrahan et al.

[11] Patent Number: 5,209,755
[45] Date of Patent: May 11, 1993

[54] DERMAL EXCISER

[76] Inventors: Stella Abrahan; Enrique Vallota, both of 2260 Brentford Rd., San Marino, Calif. 91108

[21] Appl. No.: 893,731

[22] Filed: Jun. 5, 1992

[51] Int. Cl.$^5$ ............................................. A61B 10/00
[52] U.S. Cl. ........................................ 606/132; 606/1; 606/131; 606/205; 606/206; 606/207; 606/208; 606/182; 606/183
[58] Field of Search ...................... 606/1, 9, 39, 45, 46, 606/51, 52, 110, 113, 114, 127, 128, 131, 132, 167, 170, 172, 182–185, 205–210

[56] References Cited
U.S. PATENT DOCUMENTS

| | | | |
|---|---|---|---|
| 86,016 | 1/1869 | Howell | 606/206 |
| 100,210 | 2/1870 | Stohlman et al. | 606/172 |
| 1,127,948 | 2/1915 | Wappler | 606/170 |
| 3,208,452 | 9/1965 | Stern | 606/183 |
| 3,522,809 | 8/1970 | Cornell | 606/131 |
| 3,628,522 | 12/1971 | Kato | |
| 3,807,405 | 4/1974 | Niebel | 606/131 |
| 3,934,591 | 1/1976 | Gleason | 606/132 |
| 4,542,742 | 9/1985 | Winkelman et al. | 606/167 |
| 4,646,751 | 3/1987 | Maslanka | |
| 4,721,116 | 1/1988 | Schintgen et al. | 606/207 |
| 4,815,476 | 3/1989 | Clossick | |
| 4,887,612 | 12/1989 | Esser et al. | 606/208 |
| 4,896,678 | 1/1990 | Ogawa | |
| 4,943,295 | 7/1990 | Hartlaub et al. | 606/131 |
| 5,052,402 | 10/1991 | Bencini et al. | |
| 5,082,000 | 1/1992 | Picha et al. | |

OTHER PUBLICATIONS
Cover page and p. 441 of MUTEX products catalogue, showing a dermal punch "33-20 to 28" (at top RHS).

Primary Examiner—Stephen C. Pellegrino
Assistant Examiner—Glenn Dawson
Attorney, Agent, or Firm—Stephen Donovan

[57] ABSTRACT

A skin cutter instrument for excising ellipsoid-shaped samples of skin from a patient is disclosed. The skin cutter has a hollow tube, a spring and rod combination within the tube, an assembly with multiple pivotable joints, and two skin cutting blades. The assembly carries out a scissoring motion when the rod is pressed down, causing the blades to come together and thereby remove the skin sample. The blades can have either concave cutting surfaces, or straight cutting surfaces that are deformed into an arc shape. Either blade cutting surface configuration allows for excision of the desired ellipsoid-shaped tissue sample from the patient.

8 Claims, 2 Drawing Sheets

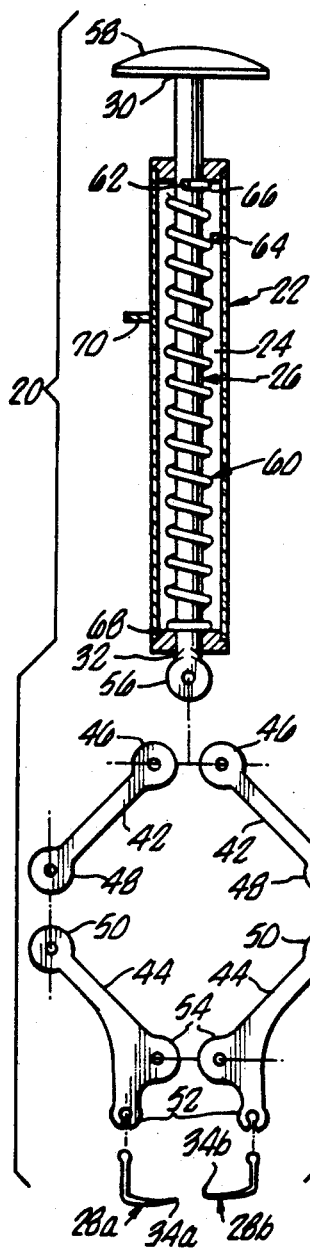
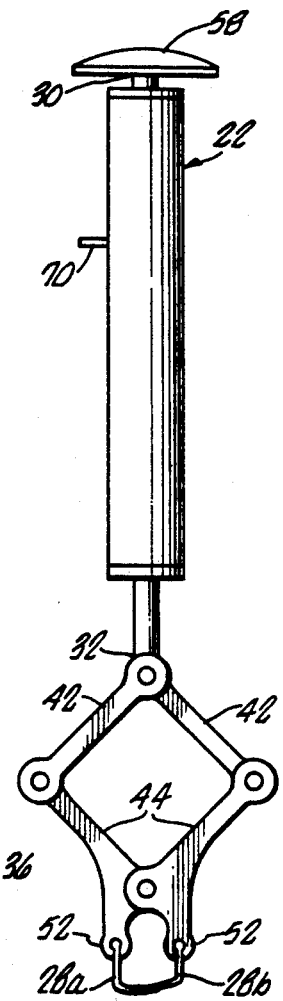
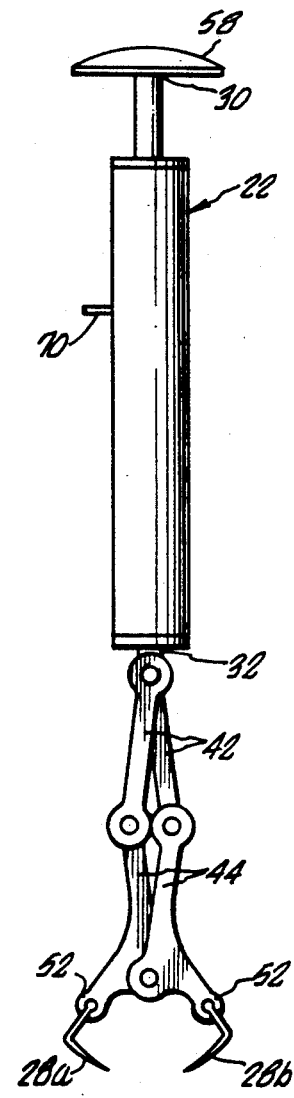
Fig. 1.  Fig. 2.  Fig. 3.
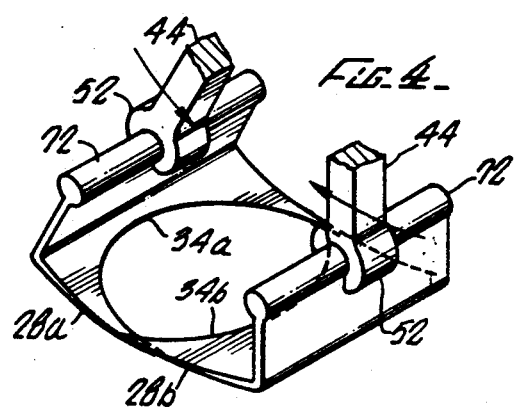
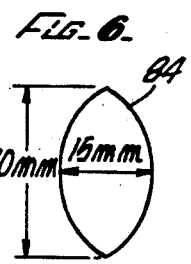
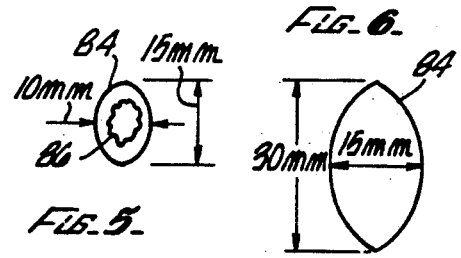
Fig. 4.  Fig. 5.  Fig. 6.

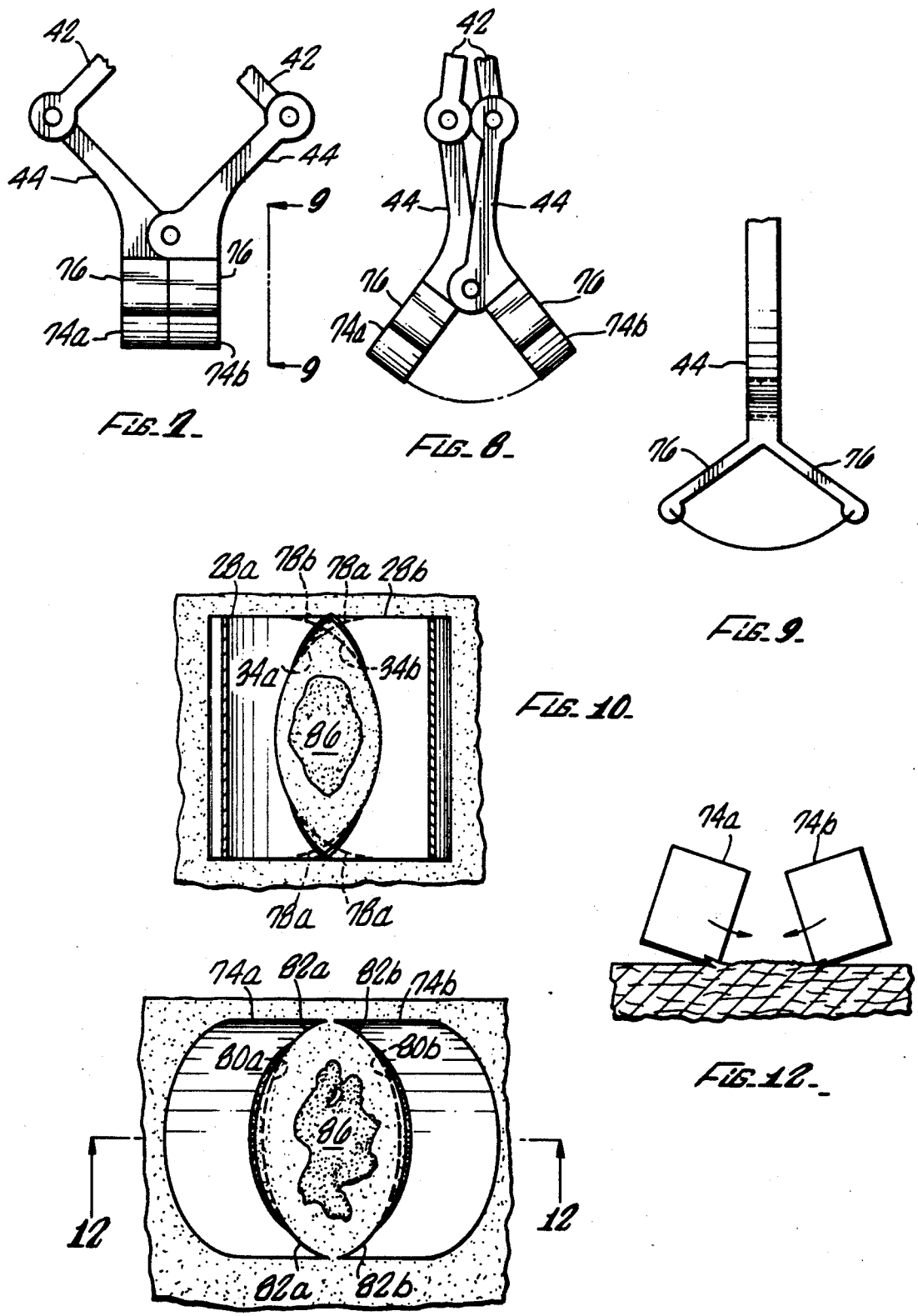

DERMAL EXCISER

BACKGROUND

We have invented a new dermal exciser or skin cutter instrument. The present invention is directed in particular to a medical instrument for excising an ellipsoid or football-shaped sample of a patients' skin.

It is very important to have an early and thorough dermatological examination of any suspected abnormality or growth on the skin. Early diagnosis, detection and then appropriate treatment can insure a full and speedy patient recovery, obviating the need for surgery or other invasive therapeutic techniques.

Dermatological examination of a patient can indicate a need to remove a sample of the patient's skin for further evaluation. Thus, a physician's examination of a patient's skin may reveal a variety of warts, moles, lesions, protuberances, calcifications, dry patches, tumors, and discolorations, all of which can be referred to as "growths", and for which laboratory study is deemed prudent. Sometimes such study shows nothing amiss. Sometimes the study indicates a need for further examination of the patient. Occasionally, examination of an excised growth indicates that the patient has melanoma, or any of a number of other disorders with may be life-threatening.

Preferably, the skin sample excised includes the entire skin growth of interest as well as a small area of the normal appearing skin around the growth, for comparative analysis. Laboratory tests can assess any influence on the normal skin by the growth. The amount of invasion or disruption of normal skin function by the growth can be used as a measure of the progress of a disease state.

It is highly preferred that when a sample of a patient's skin is removed for examination, that the skin sample have an ellipsoid or football shape. Removing a skin sample with such a shape has numerous advantages, including rapid healing of the lesion left by the excision, and formation of a regular, linear scar. Thus, when the ellipsoid-shaped skin sample of skin is removed so that the long axis of the ellipsoid-shaped skin sample is parallel to the orientation of the elastic fibers at the location on the skin from which the skin sample is removed, then a cosmetically desirable regular, linear scar will form as the lesion heals. Such a scar shape forms because the elastic fibers "close ranks" around the lesion. A further advantage of excising an ellipsoid-shaped skin sample, is that such a sample shape usually provides, in addition to the growth, sufficient normal skin for a comparative examination.

Frequently, the desired ellipsoid-shaped skin sample is removed from the patient by a physician using a scalpel. Such direct physician involvement in the actual skin sample excision is not desired because it requires direct physician involvement in a minor procedure. A busy dermatological practice can require a large number of skin sample excisions daily, particularly in sunny locations with a large number of light-skinned people, such as Southern California. The physician is thereby prevented from addressing the needs of other patients who may have more acute conditions.

Additionally, nonphysician staff are prohibited by most states from using a scalpel to excise skin samples. Nurses and medical assistants are though allowed to use, under physician supervision, nonscalpel methods for removal of skin samples. There is a known nonscalpel tool that can be used for excising skin samples. This is the dermal punch tool, The dermal punch tool can be used by a trained nonphysician to remove a skin sample. The punch tool is operated by placing it on the site of the patient's skin at which an excision is desired, and then pressing down quickly on the tool, resulting in the punching-out of a skin sample.

The dermal punch tool has several disadvantages and shortcomings. First, it permits removal of only a conical or cylindrical-shaped sample of skin. Skin samples so shaped tend to be difficult to section, stain and to examine microscopically. Second, use of the dermal punch tool leaves a circular skin lesion that can require suturing. Even when the skin lesion left by the dermal punch tool is small enough to heal without a need for stitches, the healed skin will typically have an unattractive irregularly-shaped scar. Additionally, the healed skin has an unsightly puckered appearance.

Third, the skin sample is difficult to remove from the cavity of the punch part of the punch tool after skin excision, because it tightly occupies the cavity of the punch. Usually, the skin sample must be pried loose with a needle or other pointed object or the punch tool is shaken vigorously to loosen the skin sample. The skin sample can thereby be damaged, or lost.

A damaged skin sample can give anomalous, or "false positive" test results. Furthermore, loss of the skin sample can be a very serious matter, because the excision cannot be repeated—the growth of interest having already been removed. More invasive procedures, such as surgery, may then be required to assist diagnosis of a potential disease state in the patient.

Fourth, the dermal punch tool permits removal of only a circular piece of skin. Sometimes, the growth on the patient's skin is not circularly-shaped. Thus, the punch tool can result in removal of only a part of the growth and of too little of the surrounding skin for an effective comparative analysis. Cutting into the possibly abnormal growth and leaving part of it behind on the patient's skin can have serious consequences. A precancerous growth can be motivated by the injury to become cancerous. Alternately, an already cancerous tissue can, due to the injury, metastasize, when cancer cells dislodged by the incomplete excision disseminate to other parts of the body.

Additionally, because the elastic fibers of the skin do not run in circular patterns, removal of a circular skin sample almost inevitably results in some distortion of the skin layers within the skin sample. This occurs even if the skin sample is easily removed from the cavity of the punch part of the dermal punch tool without damaging the skin sample. Such skin sample distortion can again make analysis and diagnosis difficult if not impossible.

Fifth, the nature of the cutting surface of the dermal punch tool causes it to become too blunt for further use after the excision of only a few skin samples.

Thus, there is a real need for a skin cutter instrument that: (1) removes an ellipsoid-shaped sample of a patient's skin; (2) facilitates a thorough and accurate laboratory examination of the excised skin sample; (3) leaves a skin lesion that can heal to a regular scar, without the need for suturing; (4) allows easy removal of an undamaged and undistorted excised skin sample from the instrument; (5) permits removal of an entire skin growth, thereby reducing the risk of a precancerous growth becoming cancerous, and of a cancerous growth metastasizing, and (6) remains sharp after multiple skin excisions.

SUMMARY

A skin cutter or dermal exciser embodying features of the present invention satisfies this need. The dermal exciser can remove an essentially undamaged, undistorted ellipsoid-shaped sample of a patient's skin quickly, easily, and without the need for a physician's direct involvement. Additionally, the lesion remaining after removal of the skin sample can heal without suturing, resulting in no scar or in only a small, regular and linear scar.

The dermal exciser used to remove an ellipsoid-shaped sample of skin from a patient has an elongated tube with a internal, longitudinal bore, a movable rod within the bore of the tube, and at least two blades that move as the rod is moved within the tube. The tube is open at both ends, and each blade has a sharp cutting surface that can easily cut through the patient's skin. The cutting surfaces of the blades come together to a closed position within the subcutaneous tissue of the skin of a patient upon excision of the ellipsoid-shaped skin sample.

The dermal exciser can also have an assembly part for coordinating movement of the blades. The assembly has a first part attached to the second end of the rod, and a second part attached to the first part of the assembly. The second part of the assembly is also attached to the blades.

Additionally, the first part of the assembly can be made up of two arms, and the second part of the assembly can be made up of two members. Each arm can be substantially identical, and each member can also be substantially identical.

Furthermore, each arm can have a first terminus and a second terminus, while each member can have three attachment sites. The first and second attachment sites are at opposite ends of each member, while the third attachment site is located between the first and second attachment sites of each member.

Functionally, both first termini of the arms can be pivotally attached at the same location to one end of the rod. The second terminus of each arm can be pivotally attached to the first attachment site of a corresponding member. The second attachment site of each member can be attached to one of the blades, and the third attachment sites of each member can be pivotally attached to each other. In this manner the three pivotable attachments allow the assembly to move from a first position where the blades are open, to a second position where the blades are closed.

The dermal exciser can also have a spring in the bore of the tube. The spring is attached to the rod at a location near the first end of the rod. The spring articulates with the rod to compressed and relaxed states, facilitating movement of the rod within the tube, much as the spring within a ball point pen's housing acts to help hold the pen nib down and then to allow retraction of the pen nib.

In a preferred embodiment, each blade has a concave cutting surface. In another preferred embodiment each blade has a straight cutting surface deformed into an arc. The blades can be made of a suitable metal, such as steel, that retains a sharp edge after multiple uses.

The dermal exciser can also have a stop bar attached to the first end of the rod, the stop bar acting to prevent the upper end of the rod from entering the bore of the tube. The tube and the rod can additionally be sterilizable and reusable.

The present invention also includes a method for using the described dermal excisers to remove an ellipsoid-shaped sample of skin. The method proceeds by pulling the rod until the blades assume an open position, placing the blades into contact with the skin of a patient, pushing the rod until the blades assume a closed position within the skin of the patient and then removing the blades from contact with the patient, thereby excising a sample of the patient's skin. Pulling again on the rod causes release of the excised sample of skin held by the blades.

The method of using the dermal exciser can have the additional steps of prior to excising the skin sample, cleaning the site chosen for skin excision with a suitable antiseptic, and of repairing the skin after the excision with, for example, sterile silk sutures or metal clips.

In the method, the blades are preferably placed in contact with the skin in a direction parallel to the direction of the elastic fibers of the skin at the chosen excision site and the blades come together within the subcutaneous layer of the skin, that is at a depth of about 5 mm.

DRAWINGS

These and other features, aspects and advantages of the present invention will become better understood from the accompanying description, the appended claims, and the accompanying drawings, where:

FIG. 1 is an exploded, partial section, side elevation view of a first embodiment of a dermal exciser embodying features of the invention;

FIG. 2 is a side elevation view of the dermal exciser showing the blades in a closed position;

FIG. 3 is a side elevation view of the dermal exciser showing the blades in an open position;

FIG. 4 is a detail perspective view of the blades and blade mounts of the dermal exciser, showing the blades approaching the closed position;

FIG. 5 is a plan view of a sample of skin removed from a patient by the dermal exciser;

FIG. 6 is a plan view of a sample of skin removed from a patient by the dermal exciser;

FIG. 7 is a partial side elevation view of a second embodiment of the dermal exciser showing the blades in a closed position;

FIG. 8 is a partial side elevation view of the second embodiment of the dermal exciser showing the blades in an open position;

FIG. 9 is view taken along line 9—9 in FIG. 7;

FIG. 10 is a plan view of the blades of the first embodiment of the dermal exciser showing the blades cutting the skin of a patient;

FIG. 11 is a plan view of the blades of the second embodiment of the dermal exciser showing the blades cutting the skin of a patient; and FIG. 12 is cross sectional view taken along line 12—12 of FIG. 11.

DESCRIPTION

Our invention is based on the finding that an ellipsoid-shaped sample of a patient's skin can be removed by a hand-held tool having two simultaneously and jointly operated blades with particular blade cutting surface configurations.

As shown by FIG. 1, a dermal exciser 20 embodying features of the invention has an elongated tube or housing 22 with a longitudinal bore 24, a displaceable rod 26 within the bore 24 of the tube 22, and two blades 28a and 28b. Both blades are operably associated with the rod 26, so that movement of the rod 26 causes a corresponding and proportional movement to the blades 28a and 28b. The tube 22 is open at both ends and can conveniently be about 60 mm long. The rod 26 has a first end 30 and a second end 32. Both the tube 22 and the rod 26 can be sterilizable and reusable. Blade 28a has a cutting surface 34a, while blade 28b has a cutting surface 34b, both cutting surfaces being adapted for cutting the skin of a patient.

The dermal exciser 20 preferably also has an assembly 36 for coordinating movement of the blades. The assembly has a first part 38 and a second part 40. The first part 38 is attached to the second end 32 of the rod 26. The second part 40 is attached to the first part 38, and to the blades 28a and 28b.

The first part 38 of the assembly 36 has two arms 42. The second part 40 of the assembly 36 has two members 44. Each arm 42 is substantially identical, as is each member 44, thereby facilitating a desired joint and coordinated movement of the blades 28a and 28b. Similar parts are also easier to manufacture. The arms and members can be made from and suitable plastic or material. Thin slats of metal are preferred because they can be inexpensively manufactured with the desired arm and member configurations.

Each arm 42 has a first terminus 46 and a second terminus 48, both termini being flat and rounded. Each member 44 has a first attachment site 50, a second attachment site 52 and a third attachment site 54. Only the first and third attachment sites 50 and 54 are flat and rounded. Both first termini 46 are pivotably attached to an attachment site 56 at the second end 32 of the rod 26. Attachment site 56 of the rod 26 is also flat and rounded. Flat and rounded attachment sites and termini are preferred because they permit pivotable movement of the arms and members. Other configurations of these various attachment sites and termini that permit pivotable movement can be envisaged. For example, ball and socket joints or hinged attachments are similarly suitable.

The second termini 48 of each arm 42 is pivotably attached to the corresponding first attachment site 50 of the respective member 44, as best shown by FIGS. 1 to 3. The second attachment sites 52 of each member 44 is connected to a blade 28a or 28b. Finally, the third attachment sites 54 of each member 44 are pivotably attached to each other. These three pivotable attachments (46-56, 48-50, and 54-54) permit the assembly 36 to move from a first position where the blades are open, as shown by FIG. 3, to a second position where the blades are closed, as shown by FIG. 2. Pivotable attachment can be achieved by a loose rivet and washer mechanism or by any other suitable means for attachment with a suitable play for allowing the desired pivotability.

The dermal exciser 20 can also have a stop bar 58 attached to the first end 30 of the rod 26. The stop bar acts to prevent the first end 30 of the rod 26 from entering the bore 24 of the tube 22. Thus, because pressing down on the stop bar causes the blades 28a and 28b to come together, provision of the stop bar 58 prevents the blades from being unduly compressed against each other with an attendant risk of blade breakage.

The dermal exciser 20 preferably also has a spring 60 coiled around the rod 26, and firmly joined to the rod at a location 62 near the first end 30 of the rod 26, by welding, soldering, or other suitable adhesion method. Joinder of spring to rod, allows the spring 60 to move in tandem with the rod 26, to thereby assist extension and retraction of the rod 26, and hence closing and opening of the blades 28a and 28b.

A protrusion or flap 64 secured to the inner wall of the tube 22 acts to hold a coil 66 of the spring 60 when the spring 60 is in a compressed state. The spring 60 is compressed against a flange 68 at one end of the tube 22. Thus, when the stop bar 58 is pressed down the coil 66 of the spring 60 comes to rest by abutting against the under side of the flap 64. Further compression of the spring 60 by pressing down further on the stop bar 58, causes release of the force of the compressed spring, so that the stop bar returns to its original position as shown by FIG. 3. Such spring and flap mechanisms are well known, as in ball point pens that have "click down, click up" positions.

The dermal exciser 20 can also have a lip 70 on the external surface of the tube 22. The lip 70 functions as a support or rest for an index finger of a user when the dermal exciser is held in one hand and the thumb of that user's hand is used to depress the stop bar 58. The lip 70 is positioned on the tube 22 at a location nearer to the first end 30 than to the second end 32 of the rod 26. In this manner a convenient thumb to index finger spacing is provided for the user. The lip 70 can also be in the form of a clip to allow attachment of the dermal exciser 20 to a pocket or inside of a carrying case, while still retaining the finger rest function.

The blades 28a and 28b can have a variety of configurations and yet still provide for excision of the highly desired ellipsoid-shaped skin sample. Thus, in a first embodiment of the present invention, each blade has a concave cutting surface as best shown by FIGS. 4 and 10. The proximal or non-sharp end of the blades are connected to attachment sites 52, by thickened portions 72. Thus, each portion 72 is received by its respective attachment site 52.

In a second embodiment, illustrated by FIGS. 7-9, and 11-12, blades 80a and 80b have straight cutting surfaces. FIG. 7 is a partial view of the second embodiment, showing the blades closed. FIG. 8 is a partial view of the second embodiment showing the blades open. Blades 74a and 74b, including the cutting surfaces, are deformed and held in arc configurations, as shown by FIGS. 9 and 11. FIG. 9 shows a blade being held in a deformed shape by the constant deforming pressure provided by blade holder struts 76. Alternately, the blade could be bent during manufacture and thereby able to maintain the desired arc shape of the second embodiment, without the need for any further deforming pressure. Blades so bent or deformed by the manufacturing process are held by the attachment sites 52, not by the struts 76.

The blades can be constructed of any suitable plastic or metal that provides the cutting surfaces of the desired configurations and sharpness. Metal, and in particular thin, flexible stainless steel blades, such as razor blade, are preferred because they are readily and inexpensively available from many commercial sources and can provide the requisite cutting surface shape and sharpness for an effective dermal exciser. Such a preferred blade retains its sharpness over multiple skin excision uses, and has the added advantages of being disposable and easily replaceable, should blade sterilization not be convenient or not preferred.

FIG. 3 shows a first embodiment of the invention in a ready position with the blades open. The dermal exciser is used by pulling the rod until the blades assume an open position, placing the blades into contact with the skin of a patient, and then pushing the rod until the blades assume a closed position within the skin of the patient. Pushing down on the rod also causes the spring 60 to become compressed.

The blades are then removed from contact with the patient, thereby excising a sample of the patient's skin. When release of the skin sample excised is desired, then the user simply pulls on the rod or clicks the rod to the up position, thereby relaxing the spring 60 and releasing the excised sample of skin held by the blades.

Typically, the site chosen for skin excision is cleaned with a suitable antiseptic prior to the excision. If a large skin sample has been removed, the patent's skin can be sutured after the excision.

When used, the dermal exciser is positioned so that the cutting surfaces 34a and 34b encompass the growth to be excised. The blades are also aligned parallel to the elastic fibers of the skin at that location, as shown by the skin lines. When downward pressure is exerted on the stop bar 58, the rod 26 is caused to extend from the lower open end of the tube 22. This action also causes a transmission of force through the assembly 36. The assembly 36 translates a linear movement of the rod 26 into a rotational movement of the blades. Thus, when the rod is pressed down the blades come together, to the position shown by FIG. 2. FIG. 2 also shows that when the blades come together, the arms 42 extend diagonally and outwardly from a longitudinal axis of the dermal exciser 20.

The operation of the blades to excise an ellipsoid-shaped skin sample will now be further detailed. Referring to FIGS. 4 and 10 which illustrate a first embodiment of our invention, it can be seen that each blade has a concave cutting surface. Dotted lines 78a and 78b in FIG. 10 show the position of the cutting surface of the respective blades 28a and 28b under the surface of the skin of the patient. The position of the dotted lines shows that with the first embodiment, the tips of the cutting surfaces of the blades cut into the skin first. This is also shown by the illustration of the flap of skin at the incision point. The thickening skin flaps show where the skin has already been cut. The nondotted, solid arcs of the cutting surfaces 34a and 34b show where the blade cutting surfaces have not yet cut into the skin.

In the first embodiment, the ellipsoid-shaped skin sample is removed as the blades ride over one another as shown in FIG. 4. In this manner, blades with such a configured cutting edge scoop out the desired skin sample. The riding over movement can be achieved by having one blade intersect the skin at a different angle from the other blade or by having a slightly shorter mounting member for one of the blades or by a combination of such features. The overriding or overlapping of the blades leaves a space of less than about 1 mm between the overlapping blades. Preferably the overlap space is only about 0.1 mm so as to obtain a skin sample with a good, undistorted skin layer profile.

FIGS. 11 and 12 illustrate a second embodiment of our invention. The shading of the blades in FIG. 11 shows that the blades 74a and 74b are bent into arcs in a direction towards the eye of the viewer. Dotted lines 80a and 80b in FIG. 11 show the position of the cutting surface of the respective blades 74a and 74b under the surface of the skin of the patient. The position of the dotted lines shows that with the second embodiment, the center of the cutting surfaces of the blades 74a and 74b cut into the skin first. This is also shown by the illustration of the flap of skin at the incision point. The thickening skin flaps show where the skin has already been cut. The nondotted, solid arcs of the cutting surfaces 82a and 82b show where the blade cutting surfaces have not yet cut into the skin.

A incision of the patient's skin is made by each blade. The blades are positioned parallel to the skin lines formed by elastic skin fibers at the selected excision site. The cutting surfaces of each blade preferably makes an incision to a depth of about 5 mm, thereby cutting into the subcutaneous tissue layer. Thus, the blades come together to a closed position within the subcutaneous tissue upon excising an ellipsoid-shaped sample of the patient's tissue. Incision to this depth is desired to appropriately assess a benign or malignant nature of the growth excised. Tumor thickness or invasiveness of the skin is a direct measure of the progress of a cancer such as melanoma. Deeper incisions can be made where a growth appears particularly invasive, and total growth removal is indicated.

An ellipsoid-shaped sample of skin 84 excised by the dermal exciser 20, has a length that is about 50% greater than its width. The skin sample 84 preferably encompasses an entire growth 86. Thus, skin sample sizes removed can be, for example, about 5 mm wide by about 10 mm long by about 5 mm deep, or about 10 mm wide by about 15 mm long by about 5 mm deep, or about 15 mm wide by about 30 mm long by about 5 mm deep, as shown by FIGS. 5 and 6. Various blades sizes within the scope of the present invention can be used to achieve these and other sample sizes. Thus, the blades can have cutting surfaces measuring from about 5 mm to about 40 mm long.

Dermal excisers according to the present invention have many advantages, including the following:

1. There is obtained an ellipsoid-shaped skin sample with little or no distortion, tearing or mixing of the tissue layers making up the skin sample removed. Laboratory and pathological examination is thereby facilitated.

2. The patient's skin lesion left after the excision it small, does not require suturing. A large lesion is easily repaired by skin suture, leaving a cosmetically desired regular, linear scar.

3. A nonphysician can be quickly trained to use the dermal exciser.

4. The excised skin sample is easily removed from the blades of the dermal exciser without damaging the skin sample.

5. The cutting surfaces of blades of the dermal exciser retain their sharpness over multiple uses.

From the foregoing it can be appreciated that the invention provides a medical instrument of simple construction and operation. Although the device is suitable for use as a disposable item, formed at a relatively low cost, other modifications and embodiments are envisioned such as a sterilizable and reusable device and/or with exchangeable blades.

Although the present invention has been described in considerable detail with regard to certain preferred embodiments, other embodiments within the scope of the claims are possible. For example, the assembly can be constructed with more or fewer pivoting attachment points. These and other modifications and embodiments may be apparent to those skilled in the art without departing from its spirit.

Therefore, the spirit and scope of the appended claims should not be limited to the description of the preferred embodiments or versions contained herein.

We claim:

1. A skin cutter for removing an ellipsoid-shaped sample of skin from a patient, comprising:
    (a) an elongated tube with a longitudinal bore, an inner wall and an external surface;
    (b) a moveable rod disposed within the bore of the tube, the rod having a first end and a second end;
    (c) a stop bar attached to the first end of the rod, the stop bar acting to prevent the first end of the rod from entering the bore of the tube;
    (d) a compressible spring within the bore of the tube, the spring being attached to the rod at a location near the first end of the rod;
    (e) a flap secured to the inner wall of the elongated tube, the flap being adapted for holding the spring in place when the spring is in a compressed state.
    (f) a lip attached to the external surface of the tube adapted for supporting an index finger of a user of the dermal exciser;
    (g) a plurality of blades, each blade having a cutting surface capable of cutting the skin; and
    (h) an assembly for coordinating movement of the blades, the assembly having a first part attached to the second end of the rod, and a second part of the assembly attached to the first part of the assembly, the second part of the assembly also being attached to the blades,
    whereby the skin cutter can remove an ellipsoid-shaped sample of skin from a patient.

2. The skin cutter of claim 1, wherein the assembly has the following structure:
    (a) the first part of the assembly comprises two arms;
    (b) the second part of the assembly comprises two members;
    (c) each arm of the first part of the assembly is substantially identical;
    (d) each member of the second part of the assembly is substantially identical;
    (e) each arm of the first part of the assembly has a first terminus and a second terminus;
    (f) each member of the second part of the assembly has three attachment sites, first and a second attachment sites at opposite ends of each member, and third attachment sites located intermediate to the first and second attachment sites of each member;
    (g) both first termini of the arms of the first part of the assembly are pivotally attached at the same location to the second end of the moveable rod;
    (h) the second terminus of each arm of the first part of the assembly is pivotally attached to the first attachment site of a corresponding member of the second part of the assembly;
    (i) the second attachment site of each member of the second part of the assembly is attached to one of the blades, and
    (j) the third attachment sites of each member of the second part of the assembly are pivotally attached to each other,
    whereby the three pivotable attachments allow the assembly to move from a first position where the blades are open, to a second position where the blades are closed.

3. A method for using a dermal exciser to remove an ellipsoid-shaped sample of skin, wherein the dermal exciser comprises:
    (a) an elongated tube with a longitudinal bore;
    (b) a movable rod disposed within the bore of the tube, the rod having a first end and a second end; and
    (c) a plurality of blades operably associated with the rod, each blade having a cutting surface capable of cutting the skin;
    the method comprising the steps of:
    (1) pulling the rod until the blades assume an open position;
    (2) placing the blades into contact with the skin of a patient;
    (3) pushing the rod until the blades assume a closed position within the skin of the patient;
    (4) removing the blades from contact with the patient, thereby excising an ellipsoid-shaped sample of the patient's skin; and
    (5) pulling the rod, as in step (1) above, thereby releasing the excised sample of skin held by the blades.

4. The method of claim 3, further comprising the step of:
    prior to step (2), cleaning the chosen site for skin excision with a suitable antiseptic.

5. The method of claim 3, further comprising the step of suturing the skin after step (4).

6. The method of claim 3, wherein in step (2) the blades are placed in contact with the skin in a direction parallel to the direction of the elastic fibers of the skin at the chosen skin excision site.

7. The method of claim 3, wherein in step (3) the blades come together within the skin at a depth of about 5 mm.

8. The method of claim 3, wherein the dermal exciser further comprises a spring coiled around the rod, and wherein during step (3) the spring is compressed, and in step (5) the spring is relaxed.

* * * * *